United States Patent [19]

Francis et al.

[11] 4,220,159
[45] Sep. 2, 1980

[54] ELECTRODE

[75] Inventors: Howard T. Francis, Park Forest; Robert J. Abele, Northbrook; Kenneth E. Pawlak, Mundelein, all of Ill.

[73] Assignee: Biomedical International Company, River Grove, Ill.

[21] Appl. No.: 679,656

[22] Filed: Apr. 23, 1976

Related U.S. Application Data

[63] Continuation-in-part of Ser. No. 249,135, May 1, 1972, abandoned.

[51] Int. Cl.$^2$ .............................................. A61B 5/04
[52] U.S. Cl. ................................. 128/639; 204/195 B
[58] Field of Search ............... 128/2.06 E, 2.1 E, 2 E, 128/404, 405, 410, 411, 416–418, DIG. 4, 639–641, 644, 783, 798, 802, 803; 204/195 B, 195 L, 195 M

[56] References Cited

U.S. PATENT DOCUMENTS

| 1,662,446 | 3/1928 | Wappler | 128/416 |
|---|---|---|---|
| 2,621,657 | 12/1952 | Leech | 128/417 |
| 3,508,541 | 4/1970 | Westbrook | 128/2.1 E |
| 3,590,810 | 7/1971 | Kopecky | 128/2.06 E |
| 3,659,614 | 5/1972 | Jankelson | 128/410 |
| 3,689,393 | 9/1972 | Davis | 204/195 B |

FOREIGN PATENT DOCUMENTS

| 166446 | 1/1963 | U.S.S.R. | 128/2.1 E |
|---|---|---|---|
| 176033 | 12/1965 | U.S.S.R. | 128/417 |
| 216902 | 4/1968 | U.S.S.R. | 128/2.1 E |

OTHER PUBLICATIONS

*Hackh's Chemical Dictionary*, 4th Edition, 1969, pp. 363 & 624, McGraw Hill Book Co., New York, N.Y.
Geddes et al., *Principles of Applied Biomedical Instrumentation*, pp. 211, 212, 256, 257, 1968, J. Wiley and Sons.

*Primary Examiner*—Lee S. Cohen

[57] ABSTRACT

An electrode for use in cooperation with a signal-receiving apparatus is the subject matter of this invention. The electrode receives an electrical signal from a subject, which signal is then observed. The electrode includes an electrical half cell. The half cell includes a metal and an electrolyte solution. A diaphragm holds the electrolyte in contact with the metal. The diaphragm is sufficiently permeable to allow ionic conduction between the surface of a subject and the electrolyte.

15 Claims, 4 Drawing Figures

ELECTRODE

CROSS-REFERENCE TO RELATED APPLICATION

This invention is a continuation-in-part of the applicants' application, Ser. No. 249,135, filed May 1, 1972, entitled ELECTRODE now abandoned.

BACKGROUND OF THE INVENTION

Electrical measurements are used in monitoring a wide variety of functions. The monitoring of physiological functions, especially those of mammals, has gained wide acceptance in the biomedical area. In order to have a continuous record for certain testing, it is necessary to secure the electrode to a subject for a prolonged period of time. Typical situations in which there is continuous monitoring are; cardiac patients in "intensive care wards of hospitals", astronauts during flights and pre-flight training, and mammals used in closely-regulated scientific experiments. These measurements are often used for electrocardiograms, electromyograms and electroencephalograms, as well as other electrical measurements.

It is recognized that a good electrode has certain important aspects, such as, low impedance and electrical stability. Inasmuch as the electrode operates as a half cell, the half cell potential must be stable. The primary purpose of the electrode is the faithful transmission of signals from a subject to a recording and/or observing apparatus.

When a heretofore-known electrode is used on a mammal, it is necessary to prepare the area of the skin upon which the electrode is to be positioned. Ordinarily, the skin is first cleaned; then it is often abraded to remove any dead skin which may impede proper transmittal of the electrical signal to the electrode. A suitable electrolyte, generally in a gel form, is placed on the subject's skin. The electrode is placed on the gel, forming a half cell, so that electrical signals are carried to a suitable recording and/or observing apparatus through well-known electrical circuitry.

A common electrode construction is one which utilizes a silver-silver chloride-chloride ion half cell. The silver-silver chloride-chloride ion half cell is generally formed either by compressing a mixture of silver and silver chloride powders and placing the compressed mixture in contact with a suitable electrolyte, or by forming a half cell by first electrochemically converting the surface of a silver member to a silver chloride layer and placing the silver chloride layer into contact with an electrolyte.

These known electrodes generally have performed satisfactorily in many applications. However, these known electrodes have certain undesirable properties. The electrolyte which is placed in contact with a patient's skin is generally in gel or paste form. The paste is messy to handle, both for the operator and for the patient. The preparation technique causes irritation to the patient, especially when the skin is abraded for a good electrical contact. When prolonged readings are to be taken, the paste tends to dry, causing the impedance to increase at the electrode skin interface, thereby degrading the observed signal and resulting in a failure to make a faithful transmission of the physiologically-generated signal. Furthermore, the electrical characteristics of these electrodes vary from electrode to electrode, and the measurements are limited to use with an AC amplifier. It has also been observed that there are in certain well-known electrodes drifts in potential or changes at an erratic rate in relation to time. This drifting causes errors in measurement of signals and thereby gives a distorted view of the physiological signal-generating organ or body portion. A further problem which accompanies certain known electrodes is that the silver chloride cannot be kept in contact with a patient's skin for a prolonged time without causing irritation due to silver migration. When the known electrodes are used on a given patient for a prolonged period, the electrodes are often relocated several times a day, causing discomfort to the patient and affecting the observed signal.

SUMMARY OF THE INVENTION

The present electrode does not require the use of a paste or gel between a surface and the electrode. It is an electrode which establishes a stable half cell potential between a metal and an electrolyte which is an ionic solution. The electrode includes a container for an electrolyte. The container has a permeable membrane on at least one side, which membrane is adapted for engagement with a surface from which an electrical signal is to be observed. The electrode also includes a solid metal, which is in electrochemical equilibrium with the electrolyte. The solid metal is connected to an electrical conductor, which is adapted for connection to an apparatus for observing and/or recording the signal detected at the surface of a subject.

The electrical half cell potential of the electrode is defined by the metal-metal ion interface within the electrode. It is important to note that the electrical half cell is completely sealed, except for the permeable membrane which is ion-conductive, thereby isolating the electrolyte. There is no effect upon the half cell by motion of the electrode or by exterior chemicals. The potential of the half cell is determined by the choice of solid metal and the ionic solution used as the electrolyte, and defines a constant electrical potential. Since the electrolyte does not change in its concentration and the solid metal remains constant, even violent movements of the subject have no noticeable effect on the readout at the observing and/or recording apparatus. The permeable membrane is in electrical contact with the surface of the subject, so that no paste or gel is required to establish a good contact. The permeable membrane also creates no irritation to the surface of the subject. All of which allows the electrode to be mounted on a subject for a prolonged period.

DESCRIPTION OF THE PREFERRED EMBODIMENT

Figure 1:
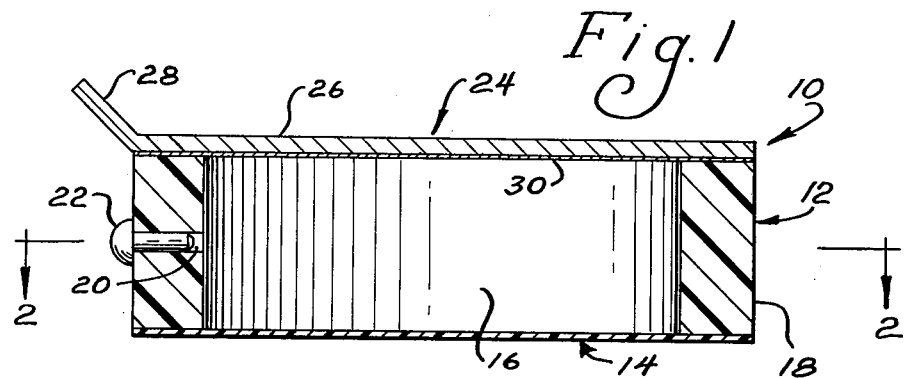
FIG. 1 is a cross-sectional view of an electrode embodying the herein-disclosed invention.
Figure 2:
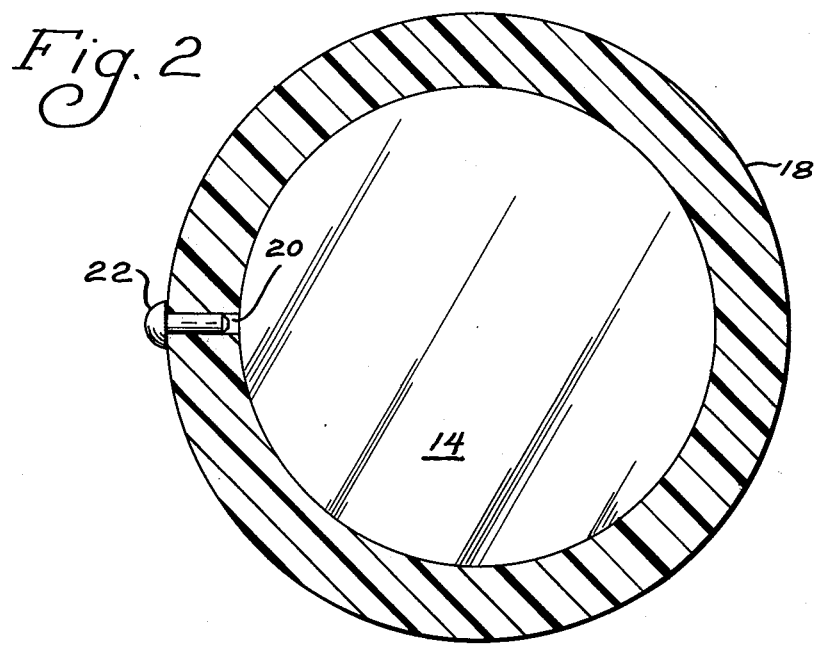
FIG. 2 is a cross-sectional view of the electrode shown in FIG. 1, taken on Line 2—2 of FIG. 1.

Referring now to the drawings, and especially to FIG. 1, an electrode which is a specific embodiment of the instant invention is generally indicated by numeral 10. The electrode generally includes a container 12, a diaphragm 14 sealingly mounted on one side of the container, and an electrolyte 16 held in the container 12 by the diaphragm 14.

The housing 12 includes a cylindrical side wall 18, which in this instance is made of acrylic resin. The side wall has a filling aperture 20, with a plug 22 in the aperture to seal closed the aperture.

The housing also includes a top 24. The top 24 includes a base 26, which in this instance is made of copper. The base 26 has formed integrally therewith a tab 28, which provides a convenient means for electrically connecting to the base 26. The inner surface of the base 25 is, in this instance, coated with a tin face 30. It is important to note that the tin face 30 is a continuous face having no porosity.

The diaphragm 14 is a permeable membrane, which acts as a porous phase separator for the electrode 10. In this instance, the diaphragm is made of conventional cellophane material; and the edges of the diaphragm are sealingly attached to the side wall 18.

The electrolyte 16 is, in this instance, a physiological saline solution of nine grams of sodium chloride per liter of water. The saline solution has free chloride ions for determining the half cell reaction with the tin of the tin face 30. In this specific embodiment of the electrode, the tin is a solid metal ion source; and the sodium chloride solution is an ionic solution which reacts with the tin to set up an oxidation-reduction reaction wherein a relatively constant electrical potential is developed, thereby providing a stable electrode. Upon contact of the electrolyte with the tin, the electrode rapidly reaches a stable potential.

It may be appreciated that the electrode 10 may be inexpensively and quickly assembled. The acrylic resin is simply formed to size with the aperture 20. The copper base 26 is formed with the tin face 30 preplaced on the copper. The top 24 is adhesively secured to the side wall 18, and the cellophane diaphragm is adhesively secured to the other end of the side wall 18. The electrolyte 16 is introduced into the interior of the container through the aperture 20. After the container has been substantially filled, the aperture 20 is plugged.

As a specific example of a given application of the subject electrode, the electrode 10 is connected to an appropriate amplifier and recording instrument in a well-known manner by means of a conventional wire, which is attached to the tab 28. The tab 28 acts as an electrical conductor for connecting the tin to an instrument. The electrical apparatus is not shown herein since it is well-known in the art, but it may be a device such as a Hewlett-Packard 1511A cardiograph. The electrode is placed on the skin of a patient, with the diaphragm in contact with the skin, and is held there by any appropriate means, such as surgical adhesive tape. Electrolyte 16 permeates diaphragm 14 to wet the outside surface of the diaphragm and thereby make good contact with the skin of the patient.

A second and third electrode, both of which are constructed in the same manner as electrode 10, are also appropriately placed on a patient, as is well-known in the art, and held in position by surgical adhesive tape. The second and third electrodes are also connected to the electrocardiograph machine. Additional electrodes may also be placed on a patient and appropriately connected to the machine, depending upon the particular application. The physiological electrical potential between two areas of the body is detected by the electrodes and transmitted to the electrocardiograph. It is important to note that even though the electrodes are secured to a patient and subjected to motion, this motion produces no effect on the electrode in view of the fact that the half cell potential is determined by the chloride ion concentration in the electrolyte. Since there is no substantial DC offset between electrode pairs and there is a great half cell stability, the electrodes may be used with a DC amplifier when desired. It should further be noted that since there is no paste or gel used in connection with the electrode, there is no drying out problem, which would cause impedance changes and the attendant deterioration of signal quality. The electrode may be positioned on a patient and intermittently connected to an electrocardiograph.

Figure 3:
FIG. 3 is a copy of a graph showing a representative readout using the subject electrode.
Figure 4:
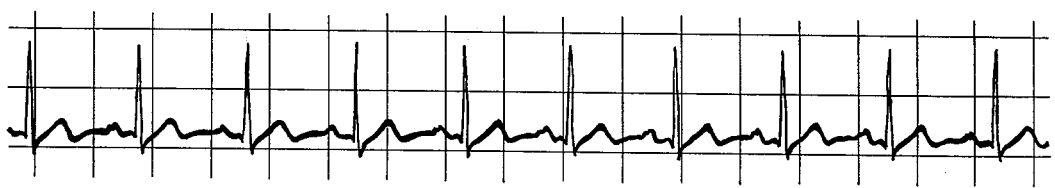
FIG. 4 is a copy of a graph showing a representative readout using a prior art electrode.

The electrode 10, used in a conventional arrangement without a paste or gel between the electrode and the patient, gives the same results over a short period of time as a conventional electrode with paste or gel, clearly demonstrating that the electrode 10 eliminates all of the problems associated with paste and provides the advantages mentioned above. The electrode 10 and two other identical electrodes were attached to a patient with surgical adhesive tape in the usual locations on a patient. The electrodes were connected to a 1511A electrocardiogram manufactured by Hewlett-Packard of Waltham, Massachusetts, in the configuration known as "Lead II", and the results were recorded. A copy of the results is shown in FIG. 3. Three conventional electrodes, known as Hewlett-Packard electrodes manufactured by said Hewlett-Packard were attached to the same patient in the same locations to provide a comparison of the effectiveness of the electrodes. A conventional paste was applied to the patient in conjunction with the conventional electrodes. The conventional electrodes were connected in the same configuration, and a copy of the results is shown in FIG. 4. Comparison of the electrocardiograms clearly demonstrates that, for short-run readings, there is no difference between the use of the conventional electrode with paste and the electrode 10 without any paste. The advantages of the electrode 10 are accentuated in a long-run observation.

During a long-run observation, which extends over several days, the electrode 10 is mounted in one location on the subject and is allowed to stay at the same location. The electrode 10 is not removed from one location and reapplied to an adjacent location several times a day, as are prior art electrodes. The constancy of location of the electrode 10 produces a constancy in the observed or recorded results for the output of the electrode, so that any variation in the results is attributable to changes in the subject under observation rather than changes in the apparatus or location of the apparatus on the subject.

Although a specific embodiment of the herein-disclosed invention has been shown and described in detail above, as is required by the applicable patent statutes, it is to be understood that one skilled in the art may make various and sundry modifications without departing from the spirit and scope of the present invention. The present invention is limited only by the appended claims.

What is claimed is:

1. A biomedical electrode for use on a subject to take electrical measurements from said subject comprising, an electrical conductor adapted for connection to an instrument for making electrical measurements, a solid metal electrically connected to the electrical conductor, a liquid ionic solution in contact with the solid metal, means for holding the ionic solution in contact with the solid metal, said means including a container having an aperture with a porous phase separator permeable by said ionic solution mounted across said aperture to retain the ionic solution, said porous phase separator having one side contacting the ionic solution and the other side being wetted by the ionic solution and being adapted for direct contact with a surface of the subject for ionic conduction between the surface and the ionic solution through the phase separator.

2. A biomedical electrode for use on a subject to take electrical measurements from said subject as defined in claim 1 wherein the solid metal is tin.

3. A biomedical electrode for use on a subject to take electrical measurements from said subject as defined in claim 1 wherein the ionic solution is physiological saline.

4. A biomedical electrode for use on a subject to take electrical measurements from said subject comprising, an electrical conductor adapted for connection to an instrument for making electrical measurements, a solid metal electrically connected to the electrical conductor, an ionic solution in contact with the solid metal, means for holding the ionic solution in contact with the solid metal, said means including a cellophane porous phase separator having one side contacting the ionic solution and the other side being adapted for direct contact with a surface of the subject for ionic conduction between the surface and the ionic solution through the phase separator.

5. A biomedical electrode for use on a subject to take electrical measurements from said subject comprising, an electrical conductor adapted for connection to an instrument for making electrical measurements, a solid metal electrically connected to the electrical conductor, a saline solution in contact with the solid metal, means for holding the saline solution in contact with the solid metal, said means including a cellophane porous phase separator having one side contacting the saline solution and the other side being adapted for direct contact with a surface of the subject for ionic conduction between the surface and the saline solution through the phase separator.

6. A biomedical electrode for use on a subject to take electrical measurements from said subject comprising, an electrical conductor adapted for connection to an instrument for making electrical measurements, a half cell connected to the electrical conductor, said half cell including a solid metal and a liquid ionic solution, a housing having an aperture on one side holding the ionic solution, and a porous phase separator mounted across said aperture and being permeable by said ionic solution to be wetted by the ionic solution and retaining the ionic solution, said porous phase separator having a wetted portion particularly adapted for direct contact with a surface of the subject for ionic conduction between the surface and the ionic solution through the phase separator.

7. A biomedical electrode for use on a subject to take electrical measurements from said subject as defined in claim 6 wherein the ionic solution is an aqueous saline solution.

8. A biomedical electrode for use on a subject to take electrical measurements from said subject as defined in claim 6 wherein the solid metal is tin.

9. A biomedical electrode for use on a subject to take electrical measurements from said subject comprising, an electrical conductor adapted for connection to an instrument for making electrical measurements, a half cell connected to the electrical conductor, said half cell including a solid metal and an ionic solution, and a cellophane porous phase separator retaining the ionic solution, said porous phase separator having a portion particularly adapted for direct contact with a surface of the subject for ionic conduction between the surface and the ionic solution through the phase separator.

10. A biomedical electrode for use on a subject to take electrical measurements from said subject comprising, an electrical conductor adapted for connection to an instrument for making electrical measurements, a half cell connected to the electrical conductor, said half cell including a solid metal and a physiological saline solution, and a cellophane porous phase separator retaining the physiological saline solution, said porous phase separator having a portion particularly adapted for direct contact with a surface of the subject for ionic conduction between the surface and the physiological saline solution through the phase separator.

11. A biomedical electrode for use on a subject to take electrical measurements from the subject comprising, a container having an open side, an ionic-conductive permeable diaphragm sealingly secured to the container closing said open side, a liquid electrolyte in said container contacting said diaphragm and permeating the diaphragm to wet the side of the diaphragm exterior of the container, said diaphragm being adapted for direct contact with a surface of a subject for ionic conduction between the surface and the electrolyte, a solid metal contacting the electrolyte, and an electrical conductor connected to said solid metal and being adapted for connection to an instrument for making electrical measurements.

12. A biomedical electrode for use on a subject to take electrical measurements from said subject as defined in claim 11 wherein the solid metal is tin.

13. A biomedical electrode for use on a subject to take electrical measurements from said subject as defined in claim 11 wherein the electrolyte is a physiological saline solution.

14. A biomedical electrode for use on a subject to take electrical measurements from the subject comprising, a container having an open side, a diaphragm of sheet cellophane sealingly secured to the container closing said open side, an electrolyte in said container contacting said diaphragm, said diaphragm being adapted for direct contact with a surface of a subject for ionic conduction between the surface and the electrolyte, a solid metal contacting the electrolyte, and an electrical conductor connected to said solid metal and being adapted for connection to an instrument for making electrical measurements.

15. A biomedical electrode for use on a subject to take electrical measurements from the subject comprising, a container having an open side, a cellophane diaphragm sealingly secured to the container closing said open side, a physiological saline solution in said container contacting said diaphragm, said diaphragm being adapted for direct contact with a surface of a subject for ionic conduction between the surface and the physiological saline solution, a solid metal contacting the physiological saline solution, and an electrical conductor connected to said solid metal and being adapted for connection to an instrument for making electrical measurements.

* * * * *